United States Patent [19]

Schewe et al.

[11] Patent Number: 4,670,469

[45] Date of Patent: Jun. 2, 1987

[54] HYDROXAMIC ACID AND PHARMACEUTICAL PREPARATIONS CONTAINING THE SAME

[75] Inventors: Tankred Schewe, Berlin; Thomas Strumpf, Potsdamm; Samuel M. Rapoport, Berlin; Dieter Zanke, Potsdamm; Jurgen Slapke; Hartmut Kuhn, both of Berlin; Horst Lyr, Eberswalde; Renate Grupe, Berlin, all of German Democratic Rep.

[73] Assignee: VEB Arzneimittelwerk Dresden, Radebeul, German Democratic Rep.

[21] Appl. No.: 584,532

[22] Filed: Feb. 28, 1984

[30] Foreign Application Priority Data

Feb. 28, 1983 [DD] German Democratic Rep. ... 248320

[51] Int. Cl.$^4$ .................. C07C 83/10; A61K 31/185; A61K 31/045; A61K 31/075
[52] U.S. Cl. ....................... 514/575; 260/500.5 H
[58] Field of Search ............... 260/500.5 H; 424/315; 514/575

[56] References Cited

U.S. PATENT DOCUMENTS

2,279,560  4/1942  Dietrich .................. 260/500.5 H
2,279,973  4/1942  Dietrich .................. 260/500.5 H

FOREIGN PATENT DOCUMENTS

0141253  4/1980  German Democratic Rep. ................................. 514/575

OTHER PUBLICATIONS

Buraczewski et al., Przemysl Chemiczny, vol. 43, No. 11, (1964), pp. 626–629.
Wise et al., J. Am. Chem. Soc., vol. 77, (1955), pp. 1058, 1059.
Epstein et al., Proc. Soc. Exptl. Biol., vol. 92, (1956), pp. 660–662.

*Primary Examiner*—J. E. Evans
*Attorney, Agent, or Firm*—Michael J. Striker

[57] ABSTRACT

Hydroxamic acids, pharmaceutical preparations containing the same, new ω(2'-naphthoxy)-alkylhydroxamic acids as well as a process for their production are disclosed. The new compounds display antiasthmatic and further pharmacologically valuable characteristics. They are prepared by reacting the corresponding carboxylic acid ester or amide with hydroxylamine or its salt under the described conditions into compounds of Formula I,

R—CO—NH—OH.

The compounds of Formula I are useful in human and veterinary medicine as medicaments the active principal of which is the inhibition of lipoxygenase, thus as antiasthmatic, antianaphylactic, antiphlogistic, antirheumatic and antithrombotic preparations.

4 Claims, No Drawings

HYDROXAMIC ACID AND PHARMACEUTICAL PREPARATIONS CONTAINING THE SAME

BACKGROUND OF THE INVENTION

The invention concerns hydroxamic acid-containing pharmaceutical preparations, new ω(2'-naphthoxy)-alkylhydroxamic acids, as well as a process for their production.

The compounds possess valuable pharmacological, particularly antiasthmatic, antianaphylactic, antiphlogistic and antithrombotic characteristics and are suitable in human and veterinary medicine for use in the therapy of bronchial asthma and other allergic illnesses, from imflammatory processes of different types as well as thrombosis.

The synthesis of hydroxamic acids from carboxylic acid derivatives and hydroxylamine is sufficiently described in the literature (L. Bauer and O. Exner, Angew. Chem. 86 419 (1974)). Therewith the long reaction period and obtained yields can generally indeed not be satisfactory.

The pharmacological activity of salicylhydroxamic acid was first described in 1976 (Opperdoes et al., Exp. Paracitol 40 198 (1976)). Salicylhydroxamic acid displays trypanocidal activity (e.g. against the cause of the African sleeping sickness, the South-American Chagas sickness as well as Nagana other tropical cattle diseases). 4-aminosalicylhydroxamic acid possesses antimycotic characteristics (G.B. 744307). Several 107 (2'-napthoxy)-alkylhydroxamic acids have already been suggested for employment as fungicides and bacteriocides (DD 141253) as well urease inhibitors (DD 149505) in agriculture. In addition, the use of hydroxynapthylhydroxamic acids in fungicidal and bacteriocidal agents (DD 140836) is known. With regard to any use of these compounds as pharmaceuticals in human and veterinary medicine, however, no statements have been found.

SUMMARY OF THE INVENTION

The aim of the present invention is to prepare pharmaceutical preparations which contain as active component hydroxamic acids having pharmacologically valuable characteristics.

The invention is therefore based upon the object of developing hydroxamic acids with antiasthmatic and further pharmacologically valuable characteristics, new ω(2'-naphthoxy)-alkylhydroxamic acids and their salts and a process for their production.

It has been discovered that hydroxamic acids of the Formula I, $$R-CO-NH-OH \quad (I)$$

in which

R is 2-hydroxyphenyl, 2-hydroxy-1-naphthyl, 1-hydroxy-2-naphthyl, 2-hydroxy-3-naphthyl, 2-aminophenyl or an ω(1'-naphthoxy)-alkyl or an ω(2'-naphthoxy)-alkyl of the Formula II

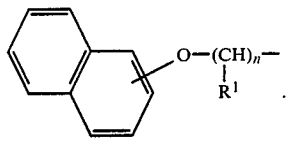

in which when n=1,
R$^1$ is straight-chain or branched alkyl with 1 to 10 carbon atoms, or phenyl, or when n=1 to 10, R$^1$ is hydrogen, possess pharmacologically valuable, particularly antiasthmatic, antiallergenic, inflammation restraining and antithrombotic characteristics, and can be used as active components of pharmaceutical preparations.

Moreover, it has been discovered that new ω(2'-naphthoxy)-alkyl hydroxamic acids of the Formula III,

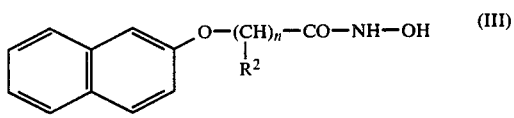

wherein when n=1,
R$^2$ is straight-chain or branched alkyl with 3 to 10 carbon atoms or substituted phenyl and when R$^2$=hydrogen, n is 4 to 9,
can be produced through reaction of ester or amides of carboxylic acids of the Formula IV,

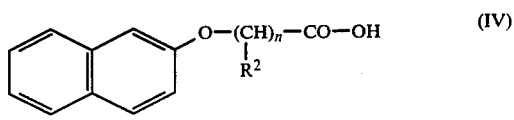

in which R$^2$ and n have the meaning given for Formula III, with hydroxylamine or a salt thereof in basic medium under the following reaction conditions:
the reaction is performed at a temperature between 20° and 100° C., or the boiling temperature of the employed solvent.
The reaction period amounts to between 20 minutes and 15 hours.

As suitable solvents for use under the reaction conditions, mention may be made of the inert organic solvents such as for example lower alcohols, acetonitrile or chloroform. Moreover, acetone, diethyl ether, di-N-butylether, acetic acid ethyl ester, 1,2-trichloroethane, dimethylformamide, dimethylsulfoxide, 1,4-dioxane, methylenechloride, nitromethane, petroleum ether, tetrachloroethylene, carbon tetrachloride, or trichloroethylene, as well as benzene, nitrobenzene, pyridine, or toluene can be employed.

The choice of the particularly advantageous solvent is also dependent upon the type of the specifically employed starting materials. For example, the reaction of a lower alkyl ester or amide of an acid of Formula IV is performed in a lower alcohol, preferably methanol. With reaction of an activated ester of Formula IV, for example acetonitrile, chloroform, dimethylformamide or acetic acid ethyl ester is used as solvent. The mentioned amide and ester of carboxylic acids of Formula IV are reacted with hydroxyl amine or a salt thereof in stoichiometric amounts or with a hydroxyl amine excess, preferably a 2-to 10-fold excess. For the reaction of the mentioned carboxylic acid derivative with hydroxyl amine salts, a stronger base in comparison with the hydroxyl amine is added in excess.

As amide of an acid of Formula IV one uses preferably the compounds that are unsubstituted at the amide nitrogen. As ester of a salt of Formula IV, preferably lower alkyl ester is employed. As activated ester, e.g. the p-nitrobenzyl-, the ethoxycarbonylmethyl-, the methoxymethyl-, the p-nitrothiophenyl- ester and preferably the cyanomethyl or p-nitrophenyl- ester of carboxylic acids of Formula IV can be used.

For the reaction of lower alkylesters or amides of carboxylic acids of Formula IV, an equivalent amount relative to the hydroxylamine salt, preferably however a 2- to 4-times excess of a base, such as e.g. sodium alcoholate or alcoholic sodium or potassium caustic soda is added.

If an activated ester, such as for example, the cyanomethylester or the p-nitrophenylester of a carboxylic acid of Formula IV is reacted, then at least a doubled equivalent amount relative to the hydroxylamine hydrochloride, of a tertiary base, such as e.g. triethylamine or pyridine, is added.

A lower alkylester is prepared for example through reaction of alkalinaphtholates, with halogen carboxylic acid esters in lower alcohols or aromates, directly or through esterification of the corresponding acids of Formula IV or through alcoholysis of the corresponding nitrile. The corresponding amide is obtained in known manner from the obtained lower alkylesters, after reaction with ammonia in known manner.

The new compounds of Formula II can if desired be transformed into their salts in known manner through reaction with an inorganic base or a metal salt.

For salt formation with compounds of Formula III, one can employ an alkalihydroxide, e.g. sodiumhydroxide or potassiumhydroxide, or alkali earth hydroxide e.g. calcium hydroxide, or a corresponding alkali- and earth alkali- halogenide.

In surprising manner it has now been determined that the compounds of Formula I are distinguished by favorable pharmacological characteristics. They can be employed in human and veterinary medicine for therapy of bronchial asthma and allergenic illnesses from inflammation and thrombosis.

A use as medicine applies also to the salts of the compounds of Formula I. Preferably, pharmacologically well compatible salts are employed. Hereunder are to be understood particularly salts with such bases, the cation of which at the dosages in question display either no or only a desired specific pharmacological activity. Moreover, it is advantageous when the salts to be employed as active substance are crystallizable and are not at all or only weakly hygroscopic. For salt formation with compounds of Formula I, one can employ for example inorganic bases, such as e.g. aqueous or aqueous/alcoholic solutions of alkali- or earth alkali- hydroxides.

The compounds of Formula I possess pharmacologically valuable particularly antiasthmatic, antiallergenic, inflammation-restraining and antithrombotic characteristics.

They display in animal experimental tests on isolated lung strips from guinea pigs a pronounced antiasthmatic effect. The testing of the mentioned pharmacological characteristics follows according to the principles of measuring techniques known from the literature, which come into use in modified form (G. M. Drazen et al. G. Clin. Invest. 63 1 (1979); M. W. Schneider and G. M. Drazen Amer. Rev. Resp. Dis. 121 835 (1980); S. S. Yen and W. Kreutner, Agents Actions 10 274 (1980); S. S. Yen Prostaglandins 22, 183 (1981)).

The compounds of Formula I effect a significant restraint on arachidonic acid-induced bronchial constriction ($1.5.10^{-5}M$ arachidonic acid) in the guinea pig lung preparations (see, Example 6). Also with the addition of a cyclooxygenase inhibitor to the measuring system this effect was unaltered, and to some extent stronger, detectably. These experimental results permit without a doubt the conclusion that the compounds of Formula I involve inhibitors of the lipoxygerase pathway of arachidonic utilization, and the above described pharmacological effect is grounded upon this mechanism of activity.

This conclusion is also confirmed in direct manner through testing of a highly purified lipoxygenase from rabbit reticulocytes (see, Example 7). The lipoxygenase from rabbit reticulocytes was obtained in electrophoretically and immunologically pure form according to a technique known from the literature (S. M. Rapoport et al. Methods in Enzymology 71, 430 (1981)). The determination of lipoxygenase activity follows at 25° C. through the polarographic measurement of the oxygen consumption by means of Clark Electrode in a standardized system.

The compounds of Formula I displayed in a final concentration of $10^{-4}M$, a 100% inhibition. Through variation of the substance concentrations, the titration curves of the inhibition and therefrom the inhibition concentrations (I-value) of the compounds can be determined.

Therewith were obtained, for example, for the 2-hydroxy-1-napthylhydroxamic acid a $I_{50}$-value of 1.6 $\mu M$, for the 2(2'-napthoxy)-acethydroxamic acid a $I_{50}$-value of 2.5 $\mu M$, and for the 2(2'-napthoxy)-2-n-nonyl-acethydroxamic acid a $I_{50}$-value 1.5 $\mu M$.

Therewith these compounds clearly surpass the BW 755 C (3-amino-N-(3-trifluoromethylphenyl)-pyrazoline-(2)) known from the prior art in effectiveness, which in tests from more recent literature is a lipoxygenase-inhibiting antiasthmatic, which under the present test conditions possesses a $I_{50}$-value of 20 $\mu M$.

Since with the new medicines the restraints of lipoxygenase has been identified as a molecular type of attack, also their influence on the thrombocyte-aggregation has been tested. The essential role of the lipoxygenase pathway for irreversibility of the thrombocyte aggregation is now known. (C. E. Dutilh et al. Prostaglandins and Medicine 6, 111 (1981)). The key role is attributed to the irreversibility of the thrombocyte aggregation in the pathogenesis of thrombotic illnesses. It is therefore a finding of extraordinary significance that the compounds of Formula I, indeed according to test conditions, either completely inhibit or make reversible the thrombocyte aggregation (see Example 8). In the experiments, the thrombocyte aggregation was triggered either by means of arachidonic acid or by means of platelet activation factor (PAF-Acether).

The inhibition of thrombocyte aggregation is likewise ascribed to the inhibition of lipoxygenase in the cells. It has thus been shown that the arachidonate-lipoxygenase activity of a microsome-free lysate of human thrombocyte concentrates is inhibited to the extent of 100% by means of 0.25 mM salicylhydroxamic acid. Moreover, it has been shown that also a series of further lipoxygenases are inhibited by means of the here described hydroxamic acids. The lipoxygenase from soybeans reacts the most insensitive, i.e. it is inhibited by means of 1 mM salicylhydroxamic acid at pH 7.4 to an extent of 60% and by means of 0.4 mM 2-hydroxy-1-napthylhydroxamic acid to an extent of 54%. In contrast, for the lipoxygenase from peas which come closer in their characteristics to human lipoxygenase, the following $I_{50}$-values are provided: salicyl hydroxamic acid, 5 µM, 2-hydroxy-1-napthylhydroxamic acid, 2 µM, 2(2'-napthoxy)-acethydroxamic acid, 2 µM. Moreover it has been shown that the formation lipoxygenase products of arachidonic acid in in vitro cultivated aorta endothelial cells of calves is hindered through 0.1 mM 2-hydroxy-1-napthylhydroxamic acids. These results permit the conclusion that the here described hydroxamic acids are universal inhibitors of lipoxygenase, wherefrom the determined pharmacological activities are attributed.

The inflammation-inhibiting activity of the compounds of Formula I is expressed, among others, by an inhibition of carrageenin edema in rat paws (see Example 9).

The antiallergenic (antianaphylactic) activity of the compounds of Formula I is shown in the test of passive cutaneous anaphylaxis. After intracutaneous application, the compounds inhibited to an extent of about 40%, i.e. the extent that is known from the literature for a selective lipoxygenase inhibitor (J. Morley et al., Agents Actions 11, 585 (1981)).

The mentioned experiments substantiate in suitable biological models the antiasthmatic, antiallergenic, antithrombotic, as well as the antiinflammatory effects.

The compounds according to the present invention are indicated in human and veterinary medicine, for example, as follows:

1. All forms of bronchial asthma including infection-dependent bronchial asthma (intrinsic asthma), the exogenous-allergic bronchial asthma (extrinsic asthma), of Type I, II and IV according to Coombs and Gell (R. R. A. Coombs and P. G. H. Gell: The classification of allergic reactions responsible for clinical hypersensitivity and disease. In: Clinical aspects of immunology, edited by P. G. H. Gell and R. R. A. Coombs, S. 575, Blackwell Scientific Publications, Oxford, 1968), the analgetic-induced bronchial asthma (aspirin-induced asthma), the loading-induced bronchial asthma (exercise-induced asthma), cold asthma, irritant-dependent bronchial asthma, and psychogenically-advanced bronchial asthma.

2. Asthmoid bronchitis and obstructive lung emphysema as well as all states of bronchial constriction, which occur as accompanying symptoms to other illnesses or secondary effects of medicinal measures, e.g. narcose complications or bronchospastic reaction after application of beta-adrenergic blocker substances.

3. Allergenic illnesses in the broadest sense, particularly:
   atopic dermatitis
   allergic rhinitis (seasonal rhinitis, perennial rhinitis but also vasomotor rhinitis
   urticaria
   angioedema
   contact dermatitis (contact eczema)
   allergic illnesses of the gastrointestinal tract.

4. All forms of thrombosis, not only for the treatment of existent thrombosis (thrombophlebitis) but also
   chronic-ischemic heart disease
   after-treatment with myocardial infarction
   chronic recurring thrombosis
   chronic thrombophlebitis 5. The use as inflammation-inhibiting medicine based upon non-steroidal antiphlogistics, whereby the compounds of Formula I are indicated with such inflammatory processes for which the customary antiphlogistics (e.g. acetylsalicylic acid, salicylate and others) which display a point of attack outside of lipoxygenase, display insufficient therapeutic effect, particularly with purulent inflammation and rheumatic illnesses.

The compounds of Formula I are suitable as active substance for oral, rectal, parenteral or percutaneous as well as aerosol- useable medicines for the treatment of various types of bronchial asthma as well as thrombosis, rheumatic, arthritic and other inflammatory illnesses.

Compounds according to the present invention providing particularly favorable pharmacological characteristics include the following:
Salicylhydroxamic acid
2-amino-benzhydroxamic acid
2-hydroxy-1-naphthylhydroxamic acid
1-hydroxy-2-naphthylhydroxamic acid
2-hydroxy-3-naphthylhydroxamic acid
2(2'-naphthoxy)-acethydroxamic acid
2(2'-naphthoxy)-2-methyl-acethydroxamic acid
2(2'-naphthoxy)-2-ethyl-acethydroxamic acid
2(2'-naphthoxy)-2-n-propyl-acethydroxamic acid
2(2'-naphthoxy)-2-i-propyl-acethydroxamic acid
2(2'-naphthoxy)2-n-butyl-acethydroxamic acid
2(2'-naphthoxy)2-n-pentyl-acethydroxamic acid
2(2'-naphthoxy)2-n-hexyl-acethydroxamic acid
2(2'-naphthoxy)2-n-nonyl-acethydroxamic acid
2(2'-naphthoxy)-2-phenyl-acethydroxamic acid
2(2'-naphthoxy)-2-P-tolyl-acethydroxamic acid
2(2'-naphthoxy)-2-P-chlorophenyl-acethydroxamic acid
3(2'-naphthoxy)-propylhydroxamic acid
4(2'-naphthoxy)-butylhydroxamic acid
5(2'-naptoxy)-valerylhydroxamic acid
7(2'-naphthoxy)-heptylhydroxamic acid
8(2'-naphthoxy)-octylhydroxamic acid
11(2'-naphthoxy)-undecanylhydroxamic acid
2(1'-naphthoxy)-acethydroxamic acid
2(1'-naphthoxy)-2-methyl-acethydroxamic acid
2(1'-naphthoxy)-2-ethyl-acethydroxamic acid The present invention includes pharmaceutical preparations which in addition to non-toxic, inert pharmaceutically suitable carrier substances contain one or more of the active substances according to the present invention.

By non-toxic, inert pharmaceutically suitable carrier substances are meant solid, semi-solid, or liquid diluting agents, fillers and formulation adjuvants of all types.

Preferred pharmaceutical preparations may be in the form of tablets, dragees, capsules, pills, granulates, suppositories, solutions, suspensions and emulsions, pastes, salves, gels, creams, lotions, powders, sprays, and aerosols.

Tablets, dragees, capsules, pills and granulates can contain in addition to the active substances, the customary carrier materials, such as (a) fillers and extenders, i.e. starchy milk sugar, cane sugar, glucose, mannite and silicic acid, (b) binding agents, e.g. carboxymethyl-cellulose, alginate, gelatin, polyvinylpyrrolidon, (c) moisture-retaining agents, e.g. glycerine, (d) effervescing agent, e.g. agar-agar, calcium carbonate, and sodium bicarbonate, (e) solution retardants, e.g. paraffin and (f) resorption-accelerators e.g. quaternary ammonium compounds, (g) wetting agents e.g. cetylalcohol, glycerinmonostearate, (h) adsorption agents e.g. kaolin and bentonite and (i) lubricants, e.g. talc, calcium- and magnesium-stearate and solid polyethyleneglycol or mixtures of the material set forth under (a) through (i).

The tablets, dragees, capsules, pills and granulates can be provided with the customary coatings, if necessary containing opalization-agent, and also be so composed that they deposit the active substance or substances only or preferably in a determined part of the intestinal tract, if necessary, delayed, whereby as embedding masses, e.g. polymer substances and waxes can be employed.

The substance or substances can, if necessary be provided with one or more of the abovementioned carrier substances, also in micro-encapsulated form.

Suppositories can contain, in addition to the active substance or substances the customary water-soluble or water-insoluble carriers, e.g., polyethyleneglycol, fat, e.g. cocoa fat and higher esters (e.g. $C_{14}$-alcohol with $C_{16}$-fatty acid or mixtures of these substances).

Salves, pastes, creams and gels can contain in addition to the active substance or substances, customary carriers, e.g. animal and plant fats, waxes, paraffins, starches, tragacanth, cellulose derivatives, polyethylglycol, silicon, bentonite, talc, silicic acid and zinc oxide or mixtures of these substances.

Sprays and powders can contain in addition to the active substance or substances, the customary carriers e.g. milk sugar, talc, silicic acid, aluminum hydroxide, calciumsilicate, and polyamide powder or mixtures of these materials. Sprays can contain, in addition, the customary propellants, e.g. chlorofluorohydrocarbons.

Solutions and emulsions can contain, in addition to the active substance or substances, customary carriers such as solvents, dissolving agents and emulsifiers, e.g. water, ethylalcohol, isopropylalcohol, ethylcarbonate, ethylacetate, benzylalcohol, benzylbenzoate, propyleneglycol, 1-3-butylene-glycol, dimethylformamide, oils, particularly cotton seed oil, peanut oil, cashew nut oil, wheat germ oil, olive oil, castor oil, and sesame oil, glycerine, glycerineformaldehyde, tetrahydrofurfurylalcohol, polyethylene glycol and fatty acid ester of sorbitane or mixtures of these substances.

For parenteral application, the solutions and emulsions can also be provided in sterile and blood-isotonic form.

Suspensions can contain, in addition to the active substance or substances, customary carriers such as liquid diluting agents, e.g. water, ethylalcohol, propyleneglycol, suspending agents, e.g. ethoxylated isostearyl alcohol, polyoxyethylenesorbite and sorbitane ester, microcrystalline-cellulose, aluminum metahydroxide, bentonite, agar-agar, or tragacenth, or mixtures thereof.

The mentioned formulations can also be provided with dyes, preservatives, as well as odor and taste improving additives, e.g. peppermint oil and eucalyptus oil, and sweeteners, e.g. saccharin.

The therapeutically active compounds should be provided in the above set forth pharmaceutical preparations preferably in a concentration of about 0.1 to 99.5 percent, most preferably from about 0.5 to 95 percent by mass of the total mixture.

The pharmaceutical preparations can also contain, in addition to the active substances according to the present invention, other pharmaceutically active substances.

The production of the above set forth pharmaceutical preparations follows the customary manner according to known techniques, e.g. by mixing of the active substance with the carrier material.

Also belonging to the present invention is the use of the active substances according to the present invention as well as the pharmaceutical preparations which contain one or more thereof in human and veterinary medicine for prevention, improvement and/or cure of the above described illnesses.

The active substance or the pharmaceutical preparation can be applied locally, orally, parenterally, intraperitoneally, and/or rectally, preferably orally, and particularly as an aerosol.

In general, it has proven to be advantageous to dispense the active substance according to the present invention in total amounts from about 10 to about 300, preferably 50 to 200 mg/kg body weight per 24 hours, if necessary in the form of several individual doses, for realization of the desired result.

It can, however, be necessary to deviate from the mentioned dosages, and indeed, depending upon the type and body weight of the object being treated, the type and seriousness of the illness, the type of preparation and the application of the medicine as well as the time period or interval within which the deviation takes place. It can thus, in several cases, be sufficient to provide less than the abovementioned amount of active substance whereas in other cases the abovementioned amount of active substance must be exceeded.

The novel features which are considered as characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

Examples of the new (2'-naphthoxy)-alkylhydroxamic acid are set forth in Table 1.

Naphthyl–O–(CH)$_n$–CO–NH–OH with R$^2$ substituent

| R$^2$ | n | M.P./°C./ |
|---|---|---|
| —C$_3$H$_7$(n) | 1 | cryst. amorph. |
| —C$_4$H$_9$(n) | 1 | 141 (D) |
| —C$_4$H$_9$(i) | 1 | cryst. amorph. |
| —C$_5$H$_{11}$(n) | 1 | 144 (D) |
| —C$_7$H$_{15}$(n) | 1 | 152 (D) |
| —C$_8$H$_{17}$(n) | 1 | 158 (D) |
| —C$_6$H$_4$—CH$_3$(p) | 1 | 117-8 (D) |
| —C$_6$H$_4$—Cl(p) | 1 | 133-4 (D) |
| —H | 4 | 130-1 (D) |
| —H | 5 | 127 (D) |
| —H | 7 | 125-6 (D) |
| —H | 9 | 122-3 (D) |

EXAMPLE 1

Production of 5(2'-naphthoxy)-valerylhydroxamic acid

To an absolute methanol solution prepared from 4.6 g sodium and 6.9 g hydroxylamine-hydrochloride, are added dropwise under stirring, 25.9 g 5(2'-naphthoxy)-valeric acid methylester (from 5(2'-naphthoxy)-valeric acid and methanol, Kp$_{1.8}$171°-2° C.) dissolved in 30 ml absolute methanol, followed by heating for 60 minutes under reflux. The reaction mixture is then cooled and the solution is compressed to dryness in a vacuum at room temperature. The residue is reacted with 500 ml water and 100 ml ether, stirred 20 minutes, after which the aqueous solution is separated and acidified with 6-n hydrochloric acid. The suspension is then extracted three times, each time with 100 ml ether. The ether solution is washed with 50 ml water and 50 ml saturated sodium chloride solution, dried over sodium sulphate, and the solvent is removed in a vacuum. After recrystallization from $H_2O$/methanol, are obtained 15.8 g of 5(2'-naphthoxy)-valerylhydroxamic acid with melting point 130°–1° C. (D).

EXAMPLE 2

Production of 2(2'-naphthoxy)-2-n-octyl-acethydroxamic acid (a) 2(2'-naphthoxy)-2-n-octyl-acetic acid ethyl ester 2.3 g sodium are dissolved in 100 ml absolute alcohol, then reacted with 14.4 g 2-naphthol and heated in a vacuum to constant weight. Thereafter are added 150 ml absolute toluene and then 87 g 2-bromodecancarboxylic acid ester.

Reaction mixture is heated at 150°–160° C. up to neutral reaction with reflux and then reacted with water, after which the organic phase is extracted with ether. The etheric solution is washed with bicarbonate, dried with magnesium sulphate, after which the solvent is discharged. One obtains after fractionation of the residue 26.8 g 2(2'-naphthoxy)-2-n-octylacetic acid ester as a weakly yellowish oil of boiling point $K_{p0.5}$ 186°–187° C.

(b) 2(2'-naphthoxy)-2-n-octyl-acetylhydroxamic acid 3.7 g of 2(2'-naphthoxy)-2-n-octyl-acetic acid ester are added to an absolute alcohol solution prepared from 2.3 g sodium and 6.9 g hydroxyl amine hydrochloride, followed by stirring at 40° C. for 8 hours. Thereafter the reaction mixture is heated a further 1 hour in a boiling water bath and the alcohol is then removed in a vacuum at room temperature. The residue is allowed to stand for 1 week and is then sucked off in a vacuum. Finally, it is washed with water and the remaining hydroxamic acid is dried. 2.9 g of 2(2'-naphthoxy)-2-n-octyl acid acetylhydroxamic acid are obtained, from $H_2O$/EtOH), and having a melting point of 158° C. (D).

EXAMPLE 3

Production of 10(2'-naphthoxy)-decanohydroxamic acid (a) 10(2'-naphthoxy)-decanoic acid-cyanomethylester A mixture of 8.5 g of 10(2'-naphthoxy)-decanoic acid (melting point 144° C., ether/petroleum ether), 2.3 g chloroacetonitrile and 3 g triethylamine in 50 ml acetic acid ethyl ester is stirred for 10 hours at 60° C. then cooled, whereupon the deposited triethylamine hydrochloride is separated. The filtrate is washed with 10 ml 1-n hydrochloric acid, twice with 15 ml each time sodium hydrogen carbonate solution, as well as 15 ml water. Therefore it is dried over sodium sulphate and the solvent is removed at 30° C. in a vacuum. 3.8 g of 10(2'-naphthoxy)-decanoic acid-cyanomethyl ester are obtained with melting point 121°–2° C. (MeOH).

(b) 10(2'-naphthoxy)-decanohydroxamic acid

A mixture of 3.5 g 10(2'-naphthoxy)-decanoic acid-cyanomethylester and 0.7 g hydroxylamine hydrochloride in 30 ml acetonitrile is reacted with 2 drops glacial acetic acid as well as 1.5 g triethylamine. The mixture is stirred for 30 minutes at room temperature, again reacted with 0.5 g hydroxylaminehydrochloride and 0.5 g triethylamine and stirred a further 12 hours at room temperature. Subsequently, the mixture is compressed in a water stream vacuum at 40° C., the residue is reacted with 30 ml water and twice with 50 ml each time of acetic acid ethylester. Thereafter the organic phase is separated and the solvent is removed in a vacuum. The residue is dissolved in 100 ml ether and then the ether solution is extracted with 10 ml of 1-n caustic soda, whereby the 10(2'-naphthoxy)-decanohydroxamic acid-Na salt is deposited crystalline. The crystals are filtered off, suspended in 30 ml absolute ether, and subsequently the suspension is reacted with dry hydrogenchloride under cooling. After repeated agitations the etheric solution is filtered and the ether is driven off in a vacuum. In this manner are obtained 2.8 g of 10(2'-naphthoxy)-decanohydroxamic acid of melting point 122°–23° C. (D)

EXAMPLE 4

Production of 2(2'-naphthoxy)2-p-tolyl-acethydroxamic acid (a) 2(2'-napthoxy)-2-p-tolyl-acetic acid-p-nitrophenyl ester To a solution of 6.5 g 2(2'-naphthoxy)-2-p-tolyl-acetic acid in 20 ml pyridine are added, portionwise and under stirring, 6.0 g trifluoroacetic acid-p-nitrophenyl-ester (prepared according to the publication of S. Yakakibara and N. Innkai, Bull. Chem. Soc. Japan 1983 (1965)). The mixture is stirred for 60 minutes at room temperature and then evaporated in a water stream vacuum at 30° C. Then 20 ml water are added to the residue after which it is extracted with 50 ml chloroform. The aqueous phase is separated and then extracted with 30 ml chloroform. The purified chloroform solutions are agitated with 20 ml 1-n hydrochloric acid, 20 ml 1-n sodium hydrogen carbonate solution and agitated twice, each time with 20 ml water. Thereafter the organic phase is separated, dried over magnesium sulphate and the solvent is discharged in a vacuum.

The residue is crystallized from methanol. The obtained 2(2'-naphthoxy)-2-p-tolyl-acetic acid-p-nitrophenyl ester melts at 104°–105° C.

(b) 2(2'-naphthoxy)-2-p-tolyl-acethydroxamic acid

To a suspension of 4.2 g of 2(2'-naphthoxy)-2-p-tolyl-acetic acid-p-nitrophenylester and 0.69 g hydroxylamine hydrochloride in 50 ml absolute chloroform are added 2.75 g triethylamine at room temperature. The clear solution is stirred for 90 minutes at room temperature, and subsequently the solvent is removed in a vacuum at 30° C. The residue is reacted with 100 ml ether and 5 ml 2-n hydrochloric acid. The ether solution is then separated, washed twice, each time with 40 ml water, and dried across sodium sulphate, after which the solvent is removed in a water stream vacuum. After recrystallization from methanol are obtained 2.7 g 2(2'-naphthoxy)-2-p-tolyl-acethydroxamic acid of melting point 117°–18° C. (D).

EXAMPLE 5

Production of 2(2'-naphthoxy)-2-n-propyl-acethydroxamic acid (a) 2(2'-naphthoxy)-2-n-propyl-acetamide A mixture of 7.5 g 2(2'-naphthoxy)-2-n-propyl-acetic acid ethyl ester ($K_{p0.2}$ 111°–112° C.) and 100 ml liquid ammonia is stirred for 4 days at room temperature in an autoclave. The ammonia is subsequently removed and the remaining residue is dried on a clay tile. After recrystallization from EtOH/H₂O one obtains 5.1 g of 2(2'-naphthoxy)-2-n-propylacetamide of melting point 126°–127° C.

(b) 2(2'-naphthoxy)-2-n-propyl-acethydroxamic acid

To a solution of 1.84 g sodium in 50 ml absolute methanol are added at 50° C. a solution of 1.82 g hydroxylamine-hydrochloride in 30 ml absolute methanol. The reaction mixture is allowed to cool down, after which the deposited sodium chloride is separated. The solution is subsequently reacted with a solution of 5.1 g 2(2'-naphthoxy)-2-n-propyl-acetamide in 50 ml methanol, and cooked for 16 hours under reflux. Thereafter it is cooled and the solution is compressed in a vacuum until dryness at room temperature. The residue is agitated with 500 ml water and 100 ml ether. The aqueous phase is separated and acidified with 2-n hydrochloric acid. The aqueous phase is then extracted three times, each time with 50 ml ether. The etheric solution is dried with magnesium sulphate and the solvent is then removed in a vacuum.

4.2 g crystalline amorphous 2(2'-naphthoxy)-2-n-propyl-acethydroxamic acid are obtained.

The pharmacological characteristics set forth above are determined with the following model systems:

EXAMPLE 6

Inhibition of arachidonic acid-induced contraction of guinea pig lung strips and tracheal rings The testing of the compounds for antiasthmatic activity follows on isolated lung strips and isolated tracheal rings from guinea pigs according to measuring methods known from the literature (supra) in modified form. The measurements follow in thermostatically controlled organ bath, isotonically using a contraction measuring arrangement with lift receiver, measuring coil, measuring amplifier (inductive measurement with the aid of a high frequency resonant circuit). The gasification follows with air. The suspension solution has the following composition: 39.46 g NaCl, 2.2 g KCl, 6.07 g Tris, 1.0 g CaCl₂, 9.9 g glucose, 1.0 ml saturated MgCl₂-solution, 43 ml 1N HCl; pH 7.4.

(a) Activity on spasm of the guinea pig lung strips, induced by exogenous arachidonic acid.

The spasm is triggered by rising concentrations of arachidonic acid (concentrated solution in ethanol, stored in N₂-atmosphere) and is cumulatively measured. For the contraction-triggering activity of arachidonic acid are provided a $ED_{50}$-value in the range from 10 $\mu M$ and a $ED_{84}$-value in the range of 25 $\mu M$, dependent upon the specifically employed lung strip preparation. The active substance caused a highly significant displacement to the right of the Dose-Activity curves for arachidonic acid, visible by a clear elevation of the $ED_{50}$- and $ED_{84}$-values. The effect can be described through the following activity index:

$$i_{50} = \frac{ED_{50} \text{ (Active-substance)} - ED_{50} \text{ (Control)}}{ED_{50} \text{ (Control)}}$$

In an analogous manner, the index $i_{84}$ is determined from the measured data.

| Active Substance | $i_{50}$ | $i_{84}$ |
|---|---|---|
| 3-tert-butyl-4-hydroxy-anisol (known), 100 $\mu M$ | 4.6 | 3.6 |

-continued

| Active Substance | $i_{50}$ | $i_{84}$ |
|---|---|---|
| nordihydroguaiaretic acid (known), 50 $\mu M$ | 6.3 | 6.5 |
| salicylhydroxamic acid, 100 $\mu M$ | 1.9 | 8.5 |
| 2(2'-naphthoxy-acethydroxamic acid, 100 $\mu M$ | 5.8 | 7.1 |

(b) Activity on the carbachol-induced spasm of guinea pig trachia

The spasms are triggered by 3.9 $\mu M$ carbachol. Subsequent addition of the active substances being tested caused strong to very strong dilatation, which already was clearly determinable with the following active substance concentrations: 100 $\mu M$ 3-tert.-butyl-4-hydroxy-anisol, 50 $\mu M$ nordihydroguaiaretic acid, 50 $\mu M$ 2('naphthoxy)-acethydroxamic acid.

(c) Activity on the basal tones of guinea pig lung strips.

Increasing concentrations of the active substance are added to the suspension medium. There occurs a dilatation, which is cumulatively measured. From the Dose-Activity-curves are provided the following parameters:

| Active Substance | $ED_{84}$ | $ED_{50}$ |
|---|---|---|
| 3-tert.butyl-4-hydroxyanisol | 130 $\mu M$ | 61 $\mu M$ |
| 2(2'-naphthoxy-acethydroxamic acid | 27 $\mu M$ | 14 $\mu M$ |

EXAMPLE 7

Inhibition of the activity of lipoxygenase from rabbit reticulocytes

The testing of compounds for antiasthmatic, antiallergenic, inflammation-inhibiting and antithrombotic activity on the basis on the inhibition of the lipoxygenase reaction of the arachidonic acid cascade follows in a molecular/pharmacological test system. The applicability of this object for the given statement of aim was established in that many active substances known from the literature address this principle for this test object (e.g. polyacetyl fatty acids, pyrazoline derivatives, among others). In contrast to the more complex systems, this molecular test system offers the advantage of testing the active substance-receptor-variation activities, independent from permeation barriers and precursor variations of the active substance, whereby the statements in Example 6 are completed and made more precise. The lipoxygenase from rabbit reticulocytes is obtained in electrophoretically and immunologically pure form according to the techniques described in the literature (supra). The determination of the lipoxygenase activity follows at 25° C. through the polorographic measurement of oxygen consumption by means of a Clark-electrode in the following system: 0.1M potassiumphosphate, pH 7.4, with 0.2 percent sodium cholate and 0.53 mM linoleic acid. The enzyme concentration in the measurement preparation came to 25 nM. The compounds to be tested are dissolved in methylglycol (freshly distilled in a vacuum) and pre-incubated for 15 minutes at the measuring temperature in the absence of sodium cholate and linoleic acid. The dilution of the compound is so selected that the final concentration in methylglycol in the pre-incubation preparation does not rise above 2 percent; under these conditions there occur no restraints in the control preparations above mentioned. The enzyme reaction is started by the addition of sodium cholate and linoleic acid. Through variation of the active substance concentration, the titration curves of the inhibition and therefrom the necessary concentrations for a 50% and an 84% inhibition ($I_{50}$- and $I_{84}$-values) are determined.

TABLE 4

Restraint of the lipoxygenase from rabbit reticulocytes

| Compound | $I_{50}$ ($\mu$M) | $I_{84}$ ($\mu$M) |
|---|---|---|
| nordihydro guaiaretic acid (known) | 0.5 | 1.6 |
| 3-tert.-butyl-4-hydroxy-anisol (known) | 160 | 600 |
| 4-nitrocatechol (known) | 4.6 | 16 |
| 5,8,11-eicosatriicacid (known) | 1.3 | |
| salicylhydroxamic acid | 20 | 60 |
| 1-hydroxy-2-naphthylhydroxamic acid | 47 | 500 |
| 2-hydroxy-1-naphthylhydroxanic acid | 1.6 | 5.2 |
| 2(1'-naphthoxy)-acethydroxamic acid | 25 | 60 |
| 2(1'-naphthoxy)-ethyl-acethydroxamic acid | 42 | 130 |
| 2(2'-naphthoxy)-acethydroxamic acid | 2.5 | 9 |
| 2(2'-naphthoxy)-2-methyl-acethydroxamic acid | 40 | 120 |
| 2(2'-naphthoxy)-2-ethyl-acethydroxamic acid | 32 | |
| 2(2'-naphthoxy)-isopropyl-acethydroxamic acid | 27 | |
| 2(2'-naphthoxy)-2-n-propyl-acethydroxamic acid | 24 | |
| 2(2'-naphthoxy)-2-n-butyl-acethydroxamic acid | 19 | |
| 2(2'-naphthoxy)-2-phenyl-acethydroxamic acid | 11 | |
| 2(2'-naphthoxy)-2-phenyl-acethydroxamic acid | 40 | |
| 2(2'-naphthoxy)-2-n-octyl-acethydroxamic acid | 2.3 | 7 |
| 2(2'-naphthoxy)-2-n-nonyl-acethydroxamic acid | 1.5 | 4.8 |
| 3(2'-naphthoxy)-n-propylhydroxamic acid | 7 | 15 |
| 4(2'-naphthoxy)-n-butyl-hydroxamic acid | 4 | 7.5 |
| 5(2'-naphthoxy)valerylhydroxamic acid | 3.5 | 6.4 |
| 8(2'-naphthoxy)-octylhydroxamic acid | 2.1 | 4.6 |

EXAMPLE 8

Restraint of the arachidonic acid- or PAF-induced thrombocyte aggregation

The testing of the compounds for antithrombotic and thrombolytic activity follows in authentic cell systems of humans in vitro. Thrombocyte-rich plasma from the blood of healthy donors is obtained by centrifugation at 1,000×g. The measurement of the thrombocyte aggregation follows by means of an aggregometer based upon diffuse light scattering or light absorption of the produced cell aggregate. The thrombocyte-rich plasma is pre-incubated at 37° C. for 3 minutes with the active substance or substances; thereafter the thrombocyte aggregation is triggered through the addition of either 0.8 mM arachidonic acid or 1 $\mu$M platelet activation factor (PAF-acether). The preparations are then stirred with a velocity of 800 rpm. Indeed according to the employed active substance concentration there occurs either a strong delay or a complete inhibition of the thrombocyte aggregation.

TABLE 5

Restraint of the arachidonic acid-induced thrombocyte aggregation

| Compound | Delay >2 min ($\mu$M) | Total Restraint ($\mu$M) |
|---|---|---|
| 4-nitrocatechol (known) | 40 | 60 |
| 3-tert.-butyl-4-hydroxyanisol (known) | 16 | 40 |
| salicylhydroxamic acid | 0.8 | 2 |
| 2-hydroxy-1-naphthyl-hydroxamic acid | 6.5 | 7 |

TABLE 5-continued

Restraint of the arachidonic acid-induced thrombocyte aggregation

| Compound | Delay >2 min ($\mu$M) | Total Restraint ($\mu$M) |
|---|---|---|
| 2(2'-naphthoxy)-acethydroxamic acid | 30 | 60 |

With the aggregation triggered by means of PAF-Acether all of the compounds tested in Table 5 effected in a concentration of 40 $\mu$M a disintegration or scattering of the initially formed cell aggregate. Identical effects are observed when in washed thrombocyte suspensions, the aggregation is triggered with 16 $\mu$M arachodonic acid. It follows from this behavior that the tested lypoxygenase inhibitors block the thrombocyte aggregation in its irreversible phase and are thereby thrombolytically active.

EXAMPLE 9

Inhibition of carrageenin edema of rat paws

The carrageenin edema is employed in international literature as a model system for inflammation-triggering (prophlogistic) procedures, and offers the possibility of in vivo testing of compounds for inflammation-inhibiting (antiphlogistic) activity.

2(2'-naphthoxy)-acethydroxamic acid is supplied to 10 rats perorally in a dose of 200 mg/kg body weight with simultaneous delivery of 0.1 ml 1% carrageenin solution per animal. The extent of the paw edema is measured hourly after the application, and compared with the control group. The following results are obtained:

TABLE 6

Restraint of the Carrageenin by means of 2(2'-naphthoxy)-acethydroxamic acid

| Time (h) | Restraint (%) |
|---|---|
| 1 | 27.3 |
| 2 | 27.3 |
| 3 | 20.2+ |
| 4 | 35.3++ |
| 5 | 21.4 |

+significant with $P < 0.01$
++significant with $P < 0.05$

EXAMPLE 10

Inhibition of histamine-induced bronchoconstriction in guinea pigs in vivo

It is sufficiently known from the literature that asthma artificially induced in guinea pigs mirrors the behavior of human bronchial asthma in suitable manner. Accordingly, this complete animal model is called upon for further experimental determination of the antiasthmatic activity of compounds of Formula I. The following describes a representative experiment with salicylhydroxamic acid (SHAM) in 60 male guinea pigs. SHAM is applied in a dose of 95 mg/kg body weight; this dose lies a power of ten below the determined values for acute toxicity ($LD_{50}$-value).

After urethane narcosis, a flexible catheter is introduced into the V. jugularis dext. of each animal. After a tracheotomy a tracheotubular needle is inserted for respiration. Then, after muscle relaxation with Pavulon, mechanical respiration follows in a Body-Plethysmograph (16 min$^{-1}$, I/E=1/1, $p_I$=20 cmH$_2$O; Muller et al., 1976; Oddoy et al., 1982).

Over a tubular flesh needle at the outwardly led tracheotubular needle, the breath volume per draw of breath is measured by means of a pneumotachograph. The values are separately integrated and registered with a light recorder.

After 3 minutes calm breathing with registration of the parameter, three animals are dosed each with 2.5 ml SHAM-solution (isotonic, 37° C., 0.1M), i.v. (SHAM was dissolved in water directly before the test by heating, and the solution was cooled quickly in an 37° C. water bath.)

After 5 minutes further observation there follows the delivery of 5 μg/kg KM Histamine i.v. for providing a submaximal bronchospasm. After a further 5 minutes, 50 μg/kg KM Histamine are injected i.v. This leads according to experience to a fast, complete bronchial spasm ("silent chest"). After registration of the breath volume over a further 5 minutes, the test is completed.

In 3 animals serving as control group, with otherwise analogous procedure, instead of SHAM, 2.5 ml isotonic NaCl-solution are applied. The results of the tests are set forth in the following table:

TABLE 7

| Animal | 2.5 ml | KM [g] | $V_{calm}$ | V-5 min after SHAM | V after 5 μg Hist. i.v. | V-5 min thereafter | V after 50 μg Hist. i.v. | V-5 min thereafter |
|---|---|---|---|---|---|---|---|---|
| 1 | SHAM | 395 | 4.9 | +0.1 | −0.4 | +0.26 | −2.4 | −0.2 |
| 2 | NaCl | 375 | 4.7 | +0.1 | −0.9 | −0.08 | −4.2 | −1.6 |
| 3 | SHAM | 470 | 4.6 | +0.2 | −2.2 | +0.48 | −4.4 | −1.0 |
| 4 | NaCl | 410 | 2.5 | +0.06 | −1.9 | −0.57 | −2.5 | −1.2 |
| 5 | SHAM | 485 | 2.63 | +0.45 | ±0 | +0.19 | −1.6 | −0.9 |
| 6 | NaCl | 555 | 5.8 | +0.08 | −1.4 | −0.84 | −5.8 | −4.8 |

The calm- and the 5-minute values are mean values (in cm amplitude) from each 5 draws of breath.

The values after the Histamine injections represent the draw of breath having the smallest volume (3rd to 5th draw of breath after injection).

TABLE 8

Measured volumes or volume changes in Percent of the starting draw volumes draw volumes

| Animal | 2.5 ml | After 5 min | After 5 μg/kg Histamine | after 5 min | after 5 μg/kg Histamine | after 5 min |
|---|---|---|---|---|---|---|
| 1 | SHAM | +2 | −8 | +5 | −49 | −04 |
| 2 | NaCl | +3 | −19 | −1 | −89 | −34 |
| 3 | SHAM | +4 | −48 | +10 | −95.7 | −22 |
| 4 | NaCl | +2 | −76 | −17 | −100 | −48 |
| 5 | SHAM | +17 | 0 | +7.2 | −62 | −35 |
| 6 | NaCl | +1 | −24 | −14 | −100 | −82.8 |

TABLE 9

Volume changes in percent from the starting breadth volume (average value for n = 3(')

| Animal | 2.5 ml | After 5 min | after 5 μg/kg Histamine | after 5 min | after 5 μg/kg Histamine | after 5 min |
|---|---|---|---|---|---|---|
| | SHAM | +7.7 | −18 | +7 | −68.9 | −20 |
| | NaCl | +2 | −39.7 | −16 | −96.3 | −54.9 |

The measured data lead to the following conclusions:

(1) The injection of the 2.5 ml volume i.v. is with guinea pigs of the mentioned size between 370–550 g obviously without recognizable activity on circulation or breath function.

(2) After i.v. injection of SHAM there is an insignificant rise in the breath volume which can indicate a certain broncho dilation activity per se.

(3) Animals pre-treated with SHAM react after histamine injections of different doses with a smaller bronchial spasm than the animals of the control group.

(4) The spontaneous regression of histamine induced bronchial spasm follows in SHAM-treated animals obviously more quickly and more extensively than in the control group.

It will be understood that each of the elements described above, or two or more together, may also find a useful application in other types of pharmaceutical usages differing from the types described above.

While the invention has been illustrated and described as embodied in hydroxamic acid and pharmaceutical preparations containing the same, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A method of treating bronchial asthma, asthmatic bronchitis, lung emphysema, allergic illnesses, inflammatory disease, or thromboses, by inhibiting the activity of lipoxygenase, which comprises the step of administering to an animal subject in need of said treatment a pharmaceutically effective amount of a compound of the Formula (I)

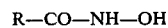

in which

R is 2-hydroxyphenyl, 2-hydroxy-1-naphthyl, 1-hydroxy-2-naphthyl, 2-hydroxy-3-naphthyl, 2-amino-phenyl or an ω(1'-naphthoxy)-alkyl or an ω(2'-naphthoxy)-alkyl of the Formula (II)

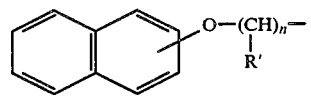

in which $R^1$ is a $C_1$ to $C_{10}$ straight or branched alkyl group, or a phenyl or a substituted phenyl group, and n is 1; or $R^1$ is hydrogen, and n is 1 to 10.

2. The method of treatment defined in claim 1 wherein the compound of the Formula (I) is administered orally.

3. The method of treatment defined in claim 2 wherein the compound of the Formula (I) is administered as an aerosol.

4. A method of treating bronchial asthma, asthmatic bronchitis, lung emphysema, allergic illnesses, inflammatory diseases, or thromboses by inhibiting the activity of lipoxygenase, which comprises the step of administering to an animal subject in need of said treatment a pharmaceutically effective amount of a compound of Formula (III)

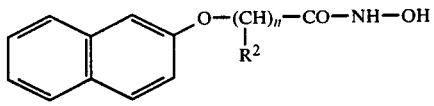

wherein
R² is a straight or branched alkyl with 3 to 10 carbon atoms or is substituted phenyl, and n is 1; or
R² is hydrogen, and n is 4 to 9.

* * * * *